United States Patent [19]
Helmig

[11] Patent Number: 5,563,352
[45] Date of Patent: Oct. 8, 1996

[54] GAS CONCENTRATION AND INJECTION SYSTEM FOR CHROMATOGRAPHIC ANALYSIS OF ORGANIC TRACE GASES

[75] Inventor: Detlev Helmig, Boulder, Colo.

[73] Assignee: University Corporation For Atmospheric Research, Boulder, Colo.

[21] Appl. No.: 369,411

[22] Filed: Jan. 6, 1995

[51] Int. Cl.$^6$ .................................................... G01N 1/00
[52] U.S. Cl. ................................. 73/863.12; 73/23.41
[58] Field of Search ........................... 73/23.41, 863.11, 73/863.12; 55/267–270; 165/2, 14, 27, 61, 154, 172

[56] References Cited

U.S. PATENT DOCUMENTS

| | | | |
|---|---|---|---|
| 1,543,449 | 6/1925 | Rust | 165/154 |
| 3,305,000 | 2/1967 | Bullen et al. | 165/27 |
| 3,525,098 | 8/1970 | Vox | 165/26 |
| 3,612,165 | 10/1971 | Haynes | 165/26 |
| 3,880,227 | 4/1975 | Bauer | 165/61 |
| 4,610,169 | 9/1986 | Clavell, Jr. | 73/863.12 |
| 4,760,538 | 7/1988 | Bock et al. | 73/64.43 |
| 5,228,514 | 7/1993 | Worden et al. | 165/155 |
| 5,259,254 | 11/1993 | Zhu et al. | 73/863.12 |

OTHER PUBLICATIONS

DuPont Brochere, "Heat Transfer", A–45967.

*Primary Examiner*—Robert Raevis
*Attorney, Agent, or Firm*—Duft, Graziano & Forest, P.C.

[57] ABSTRACT

A system for concentrating and injecting individual organic components of a gas sample into a gas chromatography system. The concentration and injection system includes a first tube longitudinally disposed within a second tube, with a columnar space therebetween. The second tube carries both a coolant and a heated fluid seriatim, thereby allowing the respective temperature conductors to directly contact the surface of the first tube and efficiently achieve the desired temperatures in the required time frame for optimum separation and sensitive detection of volatile organic compounds within the gas sample. The present system has the additional advantages of providing a flexible freezeout temperature due to the ability to regulate the cryogen flow and a flexible desorption due to the ability to regulate the temperature of the heated fluid held in a reservoir. Further, using a heated fluid coupled with the ability to regulate the fluid's temperature and flow, prevents the problem of overheating the cryotrap.

15 Claims, 2 Drawing Sheets

5,563,352

GAS CONCENTRATION AND INJECTION SYSTEM FOR CHROMATOGRAPHIC ANALYSIS OF ORGANIC TRACE GASES

FIELD OF THE INVENTION

This invention relates to the analysis of volatile organic trace gases and, in particular, to a system for concentrating and injecting the individual components of a gas sample into a gas chromatography system.

PROBLEM

It is a problem to provide a gas chromatography system with an efficient gas concentration and injection system. To analyze a volatile organic gas sample previously captured in a container, such as a stainless steel canister or solid absorbent cartridge, the sample's constituents must be concentrated into the smallest possible volume by condensing the analytes in a cryotrap, also known as a freezeout trap. The concentrate is then vaporized by rapid heating, thereby injecting the sample into a chromatographic column for maximum sensitivity and separation of individual organic species during analysis. Freezeout for a gas sample in a cryotrap is typically accomplished by flowing the sample through an inert tube that has been supercooled by liquid nitrogen or any other supercooling medium, so that the organic components within the sample are frozen onto the inner surface of the inert tube. Vaporizing the concentrated sample, also called desorption, is accomplished by rapidly heating the sample from the freezeout temperature to volatilization temperature so that the sample enters the chromatographic column as a narrow band.

One problem with existing gas chromatography techniques is the inability to distinguish individual organic constituents. The reason the constituents are indistinguishable is directly related to the relative speed with which the cryotrap is heated from the freezeout temperature to the volatilization temperature. Heating the cryotrap too slowly allows constituents to gradually bleed through the chromatographic column, thereby making individual constituents difficult to distinguish. Therefore, it is desirable to heat the cryotrap instantaneously so that the concentrate is injected into the chromatographic column instantaneously which facilitates the separation of individual organic constituents and improves the sensitivity of the measurements resulting in narrow chromatographic peaks.

Another problem with existing gas chromatography techniques is the manner in which the cryotrap is frozen and then heated, which magnifies the inability to heat the cryotrap instantaneously. Freezing the cryotrap is typically accomplished with liquid nitrogen. However, the typical cryotrap is heavily insulated from the cryogen, thereby making it difficult to precisely control the desired freezeout temperature due in part to the cryotrap's high thermal mass. Electrical filaments near the cryotrap are typically used to heat the cryotrap. However, it takes several seconds for the filaments to heat to the desired temperature, and the filaments tend to overheat or unevenly heat the cryotrap. Further, whether the heating is accomplished by electrical filaments or another heat source, the cryotrap is insulated from the heat source which inhibits rapid thermal transfer of heat to the cryotrap. To more precisely control the temperature extremes, it is desirable to have a cryotrap with a low thermal mass and flexible, but controllable, freezeout and desorption temperatures.

SOLUTION

The above described problems are solved and a technical advance achieved in the field by the gas concentration and injection system for chromatographic analysis of organic trace gases. The present invention is a system that concentrates and injects a gas sample into a chromographic column by instantaneously vaporizing the sample due to a temperature conversion from a freezeout temperature to a volatilization and desorption temperature in less than two seconds. The system configures a first tube carrying the gas sample, in a spaced relationship within a second tube carrying the cryogen and a heating fluid seriatim, without an insulating layer between the first and second tubes. The first tube has a low thermal mass and the second tube is used to flow both a coolant and then a heated fluid in turn around the first tube. Key to instantaneously converting the cryotrap's temperature from supercooled to heated is that the cryogen and the heated fluid are in direct contact with the first tube containing the gas sample. The present system has the additional advantages of providing a flexible freezeout temperature due to the ability to regulate the cryogen flow and a flexible desorption due to the ability to regulate the temperature of the heated fluid held in a reservoir. Further, using a heated fluid coupled with the ability to regulate the fluid's temperature and flow, prevents the problem of overheating the cryotrap.

DETAILED DESCRIPTION

Figure 1:
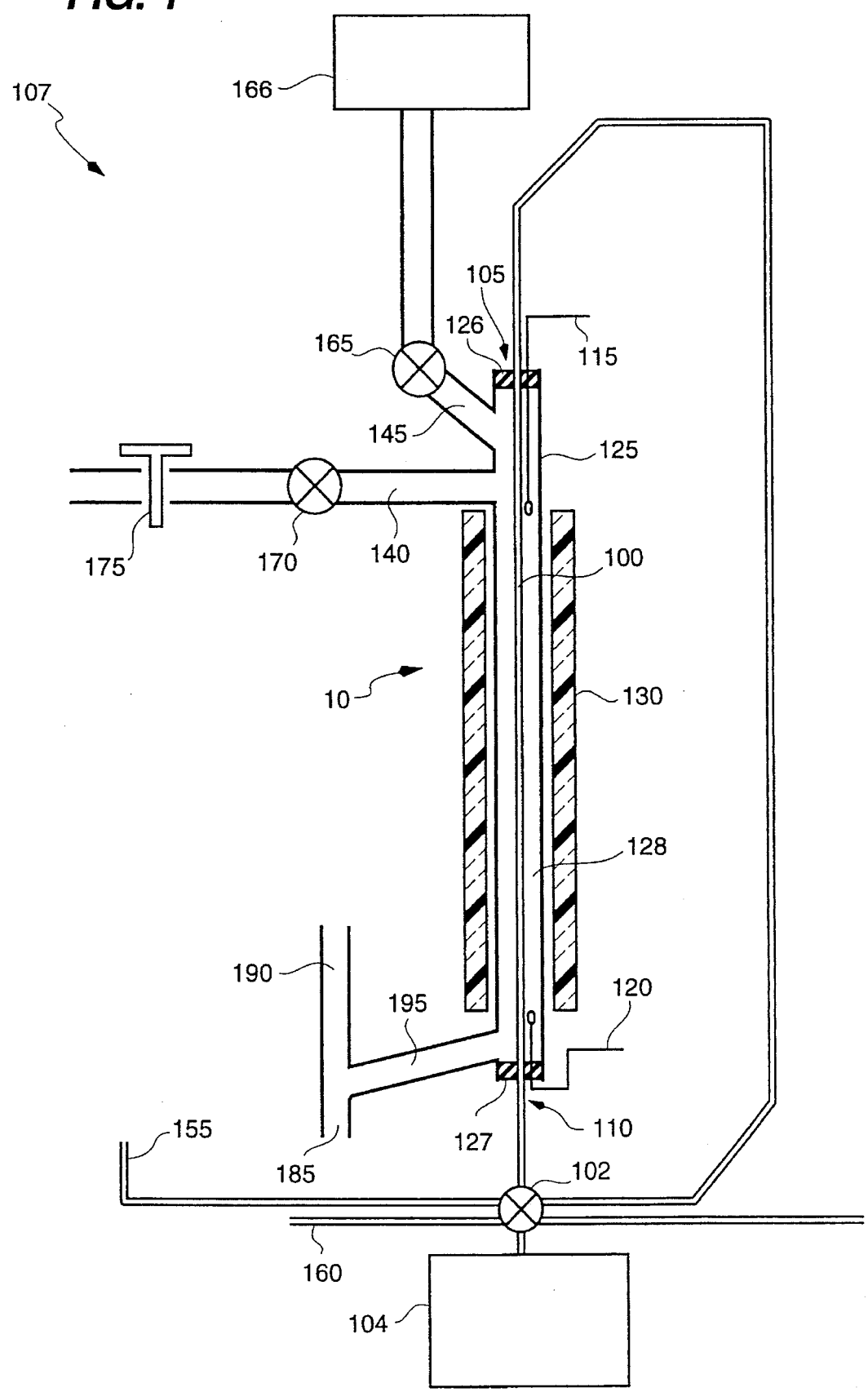
FIG. 1 illustrates the concentration and injection system incorporated in a gas chromatography system.

FIG. 1 illustrates the concentration and injection system incorporated in a cryotrap 10 of a gas chromatography system where all aspects of the concentration and injection system and the chromatographic analyzer are under the control of a programmable control system 107. Central to the cryotrap is robe 100. Tube 100 may be constructed from any material having a low thermal mass, or minimal dead volume, capable of withstanding rapid and extreme temperature variations. In general, the lower the thermal mass or more minimal the dead volume, the more efficient the thermal conductivity will be, although, separation must be maintained between the gas sample within tube 100 and the thermal source outside tube 100. Preferred materials for tube 100 include, but are not limited to, an uncoated fused silica capillary column or any related material.

The dimensions of tube 100 can affect the performance of the system in that a given volume of gas in a length of tube having a larger inner diameter and/or thicker side walls, can require more time to freeze or heat than the same volume of gas in a longer length of robe having a smaller inner diameter and thinner side walls. While the present invention is operable with a variety of materials and dimensions, the preferred embodiment for optimum gas chromatography separation and detection includes, but is not limited to, a fused silica capillary column having a length at or about 30 cm, inner diameter at or about 0.53 mm, and side wall thickness at or about 0.14 mm.

Tube 100 is longitudinally disposed in a spaced relationship within a second tube 125 so that a columnar space 128 exists therebetween. The columnar space 128 is bounded by septa 126 and 127 at opposing ends of tube 125, in a manner that allows tube 100 to pass through unobstructedly. The cross-sectional shape of the columnar space can be any geometric shape. The inner diameter of tube 125 requires enough space to house thermocouple 115 and 120 at opposing ends of columnar space 128, without touching the inner side wall of tube 125 or outer side wall of tube 100. Thermocouples 115 and 120 monitor temperature within the columnar space 128, and are connected to and controlled by control system 107. While tube 125 of the present invention is operable by being constructed from many materials having any of a variety of dimensions, the preferred embodiment includes a tube made from materials including, but not limited to, teflon or any teflon equivalent material. Preferred dimensions for tube 125 include, but are not limited to, an inner diameter at or about 4 mm to 15 mm and a length sufficient to contain a substantial portion of tube 100. The side wall thickness of tube 125 is a matter of design choice and can vary depending on the thickness and type of surrounding insulation 130.

One end of tube 125 has a coolant inlet 140 and a heated fluid inlet 145 which are controlled by valves 170 and 165 respectively. The other end of tube 125 has a combined coolant and heat exit 195 which may, but is not required to, subsequently divide into a coolant vent 190 and heated fluid vent 185 as a matter of design choice. Tube 125 is designed so that the thermal source, whether a cryogen or heated fluid, flows through the same space 128 within tube 125 at the appropriate time under the control of control system 107.

In operation, flow throttle 175 is set to allow a desired rate of cryogen flow into coolant inlet 140. Valve 170 opens and closes as needed to allow the cryogen blowoff, to enter tube 125 by way of coolant inlet 140, thereby flowing through columnar space 128. In the preferred embodiment, the cryogen blowoff is from a liquid nitrogen source (not shown), and regulated by control system 107 to achieve user-defined temperatures in a flexible range up to or about −180° C. Vent 190, from combined coolant and heat exit 195, allows the cryogen blowoff to freely vent into the atmosphere. The temperature of columnar space 128, and subsequent flow determined by flow throttle 175 and valve 170, are controlled by control system 107 based on temperature readings from thermocouples 115 and 120 respectively. The desired temperature is set, monitored, and maintained by control system 107, based on a user input temperature setpoint.

To concentrate organic constituents in tube 100, six-port valve 102 is set to allow the gas sample to pass from sample input tube 150 into tube 100 at entry point 110, so that organic compounds in the gas sample are instantaneously frozen out. Any remaining carrier gases exit tube 100 at exit point 105, passing through valve 102 to vent 155. Extracting the gas sample from a container (not shown) for input to sample input tube 150, is controlled by programmable control system 107 in any manner desired including, but not limited to, heating a solid absorbent cartridge while purging the sample with helium, or purging the contents from a hollow sample containing canister.

At the end of the concentration phase, valve 102 is set to connect tube 100 to the gas chromatography device 104, and the cryotrap 10 is backflushed by the carrier gas flow of the capillary column. The backflush path follows backflush input tube 160 through valve 102 and into the cryotrap 10 from the direction of point 105 to point 110 in tube 100. Valve 170 is closed to stop the cryogen flow and valve 165 is subsequently opened to allow a heated fluid to flow from reservoir 166 into columnar space 128 of tube 125 by way of tube 145. The heated fluid freely exits through fluid exit 185 off of combined coolant and fluid exit 195. In the preferred embodiment, the tubes 100 and 125 are vertically oriented so that the heated fluid, typically water, enters at the top of columnar space 128 near septum 126 and exits at the bottom of columnar space 128 near septum 127 by falling under its own weight. Alternatively, the heated fluid may be pumped through columnar space 128. Allowing the fluid to quickly pass through columnar space 128 maintains a continuous supply of heated fluid in a substantially uniform manner along the length of the previously cryogenically cooled tube 100. Because the heated fluid is in direct contact with the cryogenically cooled tube 100, and because tube 100 has a low thermal mass, a rapid and efficient temperature exchange results at a heating rate of approximately 125° $C./sec^{-1}$. This rate of temperature exchange instantaneously vaporizes the frozen organic constituents and injects them into the gas chromatography device 104 for separation and high resolution detection.

At the end of the injection phase, valve 165 is closed and any remaining fluid is removed from columnar space 128, in any manner including, but not limited to, gently flowing cryogen blowoff through tube 125 with the user input setpoint set at a relatively warm temperature at or about 10° C., or flowing dry ambient temperature air through tube 125.

Figure 2:
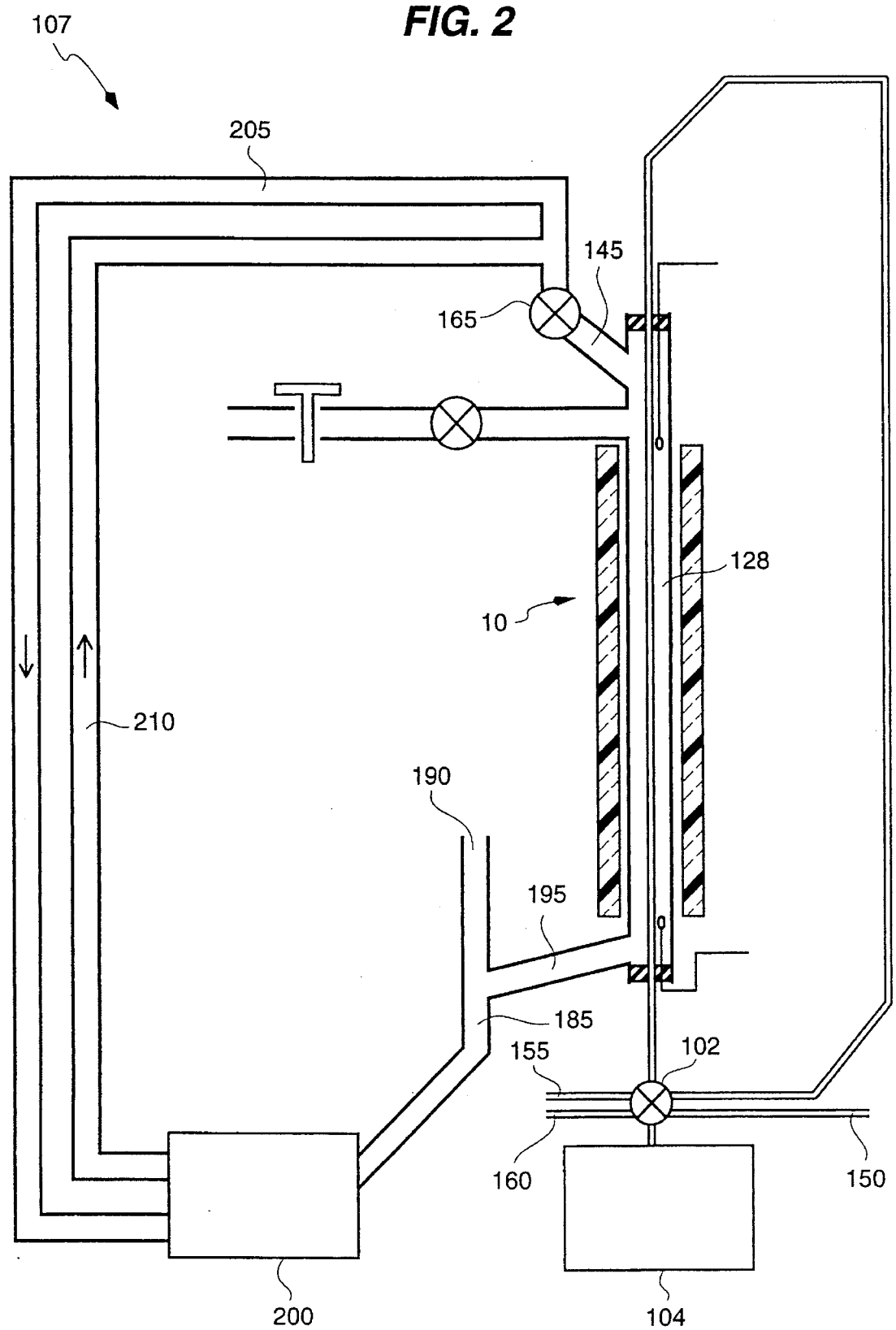
FIG. 2 illustrates an alternative embodiment for delivering a heated fluid to the concentration and injection system.

FIG. 2 illustrates an alternative embodiment of the concentration and injection system wherein the heat circulation reservoir 200 is attached to a closed system. Heat circulation reservoir 200 continuously circulates heated fluid through a ready loop defined by tubes 205 and 210 respectively during the time valve 165 is closed. When valve 165 is opened, the ready loop is broken thereby allowing heated fluid to fall through entry tube 145 into columnar space 128, and out combined exit tube 195 to return tube 185 back to circulation reservoir 200. When valve 165 is closed again, the circulation reservoir 200 continues to circulate heated fluid in the ready loop defined by tubes 205 and 210.

SUMMARY

The concentration and injection system of the present invention rapidly and efficiently heats a cryogenically cooled gas sample within 2 seconds, thereby instantaneously vaporizing the sample. Instantaneous vaporization facilitates clarity and sensitivity in separating and identifying individual organic constituents in a gas sample. Key to instantaneously converting the cryotrap's temperature from supercooled to heated is that the cryogen and the heated fluid are in direct contact with the first tube containing the gas sample. The present system has the additional advantages of providing a flexible freezeout temperature due to the ability to regulate the cryogen flow and a flexible desorption due to the ability to regulate the temperature of the heated fluid held in a reservoir. Further, using a heated fluid coupled with the ability to regulate the fluid's temperature and flow, prevents the problem of overheating the cryotrap. While specific embodiments of this invention are disclosed herein, it is expected that those skilled in the art can and will design alternate embodiments of this invention that fall within the scope of the following claims.

I claim:

1. A system for concentrating and injecting a gas sample into a gas analyzer comprising:

a first tube longitudinally disposed in a spaced relationship within at least a portion of a second tube to define a flow passageway intermediate said first tube and said portion of said second tube, said first tube being connected to a gas analyzer;

means for controllably introducing a gas sample into said first tube;

means for selectively supplying a cryogen for flow through said flow passageway to freeze-concentrate said gas sample within said first tube by direct action of said cryogen upon said first tube; and means for selectively providing a fluid heating agent for flow through said flow passageway to thaw said freeze concentrated gas sample by direct action of said fluid heating agent upon said first tube to transfer said concentrated gas sample from said first tube to said gas analyzer.

2. A system according to claim 1 wherein said providing means is capable of heating said first tube at a rate of at least 125° C. per second.

3. A system according to claim 1 wherein said first tube is an uncoated fused silica capillary column.

4. A system according to claim 1 wherein said second tube includes a teflon material.

5. A system according to claim 1 including:

means for measuring a temperature within said second tube; and means, responsive to said supplying and providing means, for monitoring and maintaining said temperature in said flow passageway.

6. A system according to claim 5 wherein said supplying means includes:

means for flowing said cryogen into a first end of said second tube, through said flow passageway along the length of said first tube, and out a second end of said second tube remote from said first end.

7. A system according to claim 1 including:

means for flushing said cryogen from said flow passageway;

means for establishing a user-defined temperature limit within said flow passageway;

means for providing a heated fluid within said flow passageway at said user-defined temperature; and means, responsive to said providing means.

8. A system according to claim 7 wherein said heated fluid is water.

9. A system according to claim 7 wherein said providing means includes:

means for flowing said heated fluid into a first end of said second tube along said flow passageway, and out a second end of said second tube remote from said first end.

10. A system according to claim 9 wherein said means for flowing is selected from the group comprising: gravity and pressurization.

11. A system according to claim 1 including:

means for controlling said system for concentrating and injecting said gas sample into said gas analyzer by way of at least one programmable control system.

12. A system for concentrating and injecting a gas sample into a gas analyzer comprising:

a first tube longitudinally disposed within a second tube, said first tube and said second tube having a columnar space therebetween;

means for flowing a cryogen through said columnar space from a first end of said second tube to a second end of said second tube along at least a portion of said first tube;

means for replacing said cryogen with a heated fluid flowing through said columnar space from a first end of said second tube to a second end of said second tube along at least a portion of said first tube for direct contact between said heated fluid and said first tube; and means for controlling said system for concentrating and injecting said gas sample into said gas analyzer by way of at least one programmable control system.

13. A method for concentrating and injecting a gas sample into a gas analyzer, said method comprising:

longitudinally disposing a first tube in a spaced relationship within at least a portion of a second tube;

cooling said first tube;

controllably introducing said gas sample into said first tube; and heating said gas sample within said first tube by direct action of a heated fluid on said first tube.

flushing a cryogen from said second tube;

establishing a user-defined temperature within said second tube;

maintaining a heated fluid at said user-defined temperature;

controllably introducing said heated fluid into said space between said first tube and said second tube; and monitoring and maintaining said user-defined temperature in said space between said first tube and said second tube, in response to controllably introducing said cryogen.

14. A method according to claim 13 wherein said step of controllably introducing includes:

flowing said heated fluid into a first end of said second tube along the length of said first tube, and out a second end of said second tube opposite said first end.

15. A method for concentrating and injecting a gas sample into a gas analyzer, said method comprising:

longitudinally disposing a first tube within a second tube, said first tube and said second tube having a columnar space therebetween;

flowing a cryogen through said columnar space from a first end of said second tube to a second end of said second tube along at least a portion of said first tube said cryogen being in direct contact with said first tube along said portion;

replacing said cryogen with a heated fluid flowing through said columnar space from a first end of said second tube to a second end of said second tube along said portion, said heated fluid being in direct contact with said first tube along said portion; and controlling said system for concentrating and injecting said gas sample and said gas analyzer by way of at least one programmable control system.

\* \* \* \* \*

UNITED STATES PATENT AND TRADEMARK OFFICE
CERTIFICATE OF CORRECTION

PATENT NO. : 5,563,352

DATED : October 8, 1996

INVENTOR(S) : DETLEV

It is certified that error appears in the above-identified patent and that said Letters Patent is hereby corrected as shown below:

Column 4, line 16, delete "see" and substitute --sec--.

Signed and Sealed this

Twenty-ninth Day of April, 1997

Attest:

Attesting Officer

BRUCE LEHMAN

Commissioner of Patents and Trademarks